(12) United States Patent
Duault et al.

(10) Patent No.: US 8,955,373 B2
(45) Date of Patent: Feb. 17, 2015

(54) EXHAUST SENSOR FOR AN INTERNAL COMBUSTION ENGINE

(75) Inventors: Frederic Duault, Decines (FR); Stephane Raquin, Villefranche sur Saone (FR)

(73) Assignee: Electricfil Automotive, Miribel (FR)

( * ) Notice: Subject to any disclaimer, the term of this patent is extended or adjusted under 35 U.S.C. 154(b) by 0 days.

(21) Appl. No.: 14/237,773

(22) PCT Filed: Aug. 7, 2012

(86) PCT No.: PCT/FR2012/051860
§ 371 (c)(1),
(2), (4) Date: Feb. 7, 2014

(87) PCT Pub. No.: WO2013/021135
PCT Pub. Date: Feb. 14, 2013

(65) Prior Publication Data
US 2014/0174167 A1   Jun. 26, 2014

(30) Foreign Application Priority Data

Aug. 8, 2011  (FR) ...................................... 11 57224

(51) Int. Cl.
*F02B 77/08* (2006.01)
*G01N 27/407* (2006.01)
*G01N 33/00* (2006.01)

(52) U.S. Cl.
CPC .......... *F02B 77/086* (2013.01); *G01N 27/4078* (2013.01); *G01N 33/0037* (2013.01)
USPC ...................................... 73/114.69; 73/23.31

(58) Field of Classification Search
USPC ................................. 73/23.31, 31.05, 114.69
See application file for complete search history.

(56) References Cited

U.S. PATENT DOCUMENTS 5,329,806 A * 7/1994 McClanahan et al. ........ 73/31.05
5,616,825 A * 4/1997 Achey et al. .................. 73/23.31
(Continued)

FOREIGN PATENT DOCUMENTS

EP    0624790 A1   11/1994
GB    1199878 A    7/1970

OTHER PUBLICATIONS

International Search Report mailed Nov. 13, 2012, corresponding to PCT/FR2012/051860.

(Continued)

*Primary Examiner* — Freddie Kirkland, III
(74) *Attorney, Agent, or Firm* — Ladas & Parry LLP

(57) ABSTRACT

The present invention relates to an exhaust sensor (1) comprising a tubular support body (2) receiving a measurement probe (3), a first end of said probe extending beyond a first end of the tubular support body through an opening therein, and a second end of said probe being secured to an electrical connection connector (4) housed inside the tubular support body (2) and fitting closely against its walls. According to the invention, the measurement probe is sealed inside the tubular support body (2) and is thermally decoupled from the environment outside the tubular support body by means of an assembly of spacers (10, 11, 12, 13) made of ceramic and of glass, the spacers being threaded around the measurement probe and distributed inside the tubular support body between the electrical connection connector and the first end of the tubular support body so as to provide at least two separate cavities, said spacers providing leaktight sealing between the measurement probe and the tubular support body.

14 Claims, 1 Drawing Sheet

(56) References Cited

U.S. PATENT DOCUMENTS

| | | | |
|---|---|---|---|
| 5,955,656 A * | 9/1999 | Graser et al. | 73/23.31 |
| 6,370,946 B1 * | 4/2002 | Lacey et al. | 73/61.62 |
| 6,401,521 B1 * | 6/2002 | Nelson | 73/31.05 |
| 6,672,132 B1 | 1/2004 | Weyl et al. | |
| 6,758,082 B2 * | 7/2004 | Geier et al. | 73/31.05 |
| 6,812,710 B2 * | 11/2004 | Weyl et al. | 324/464 |
| 7,454,949 B2 * | 11/2008 | Geier et al. | 73/23.31 |
| 7,980,132 B2 * | 7/2011 | Gustin | 73/431 |
| 8,513,961 B2 * | 8/2013 | Fujita et al. | 324/693 |
| 8,579,634 B2 * | 11/2013 | Raquin et al. | 439/31 |
| 8,591,712 B2 * | 11/2013 | Hayashi et al. | 204/424 |
| 8,627,706 B2 * | 1/2014 | Wild et al. | 73/31.05 |
| 8,806,918 B2 * | 8/2014 | Yonezu et al. | 73/31.05 |
| 2006/0162422 A1 | 7/2006 | Geier et al. | |
| 2011/0004121 A1 | 1/2011 | Drubetsky et al. | |
| 2012/0131984 A1 * | 5/2012 | Raquin et al. | 73/23.31 |

OTHER PUBLICATIONS

European Official Notification dated Nov. 20, 2014, corresponding to European Patent Application No. 12758552.9.

* cited by examiner

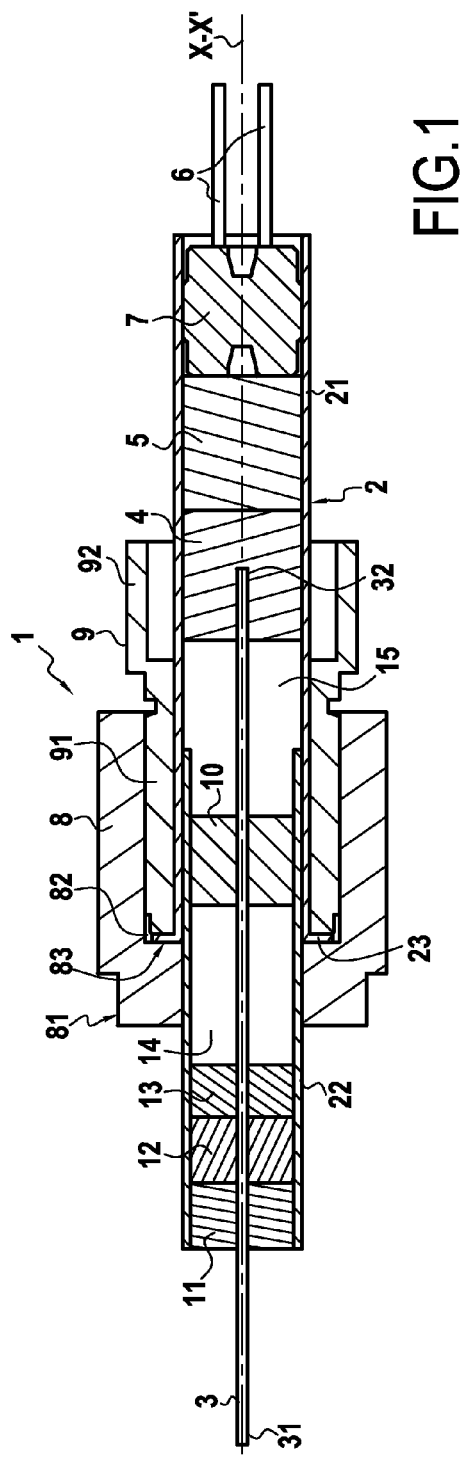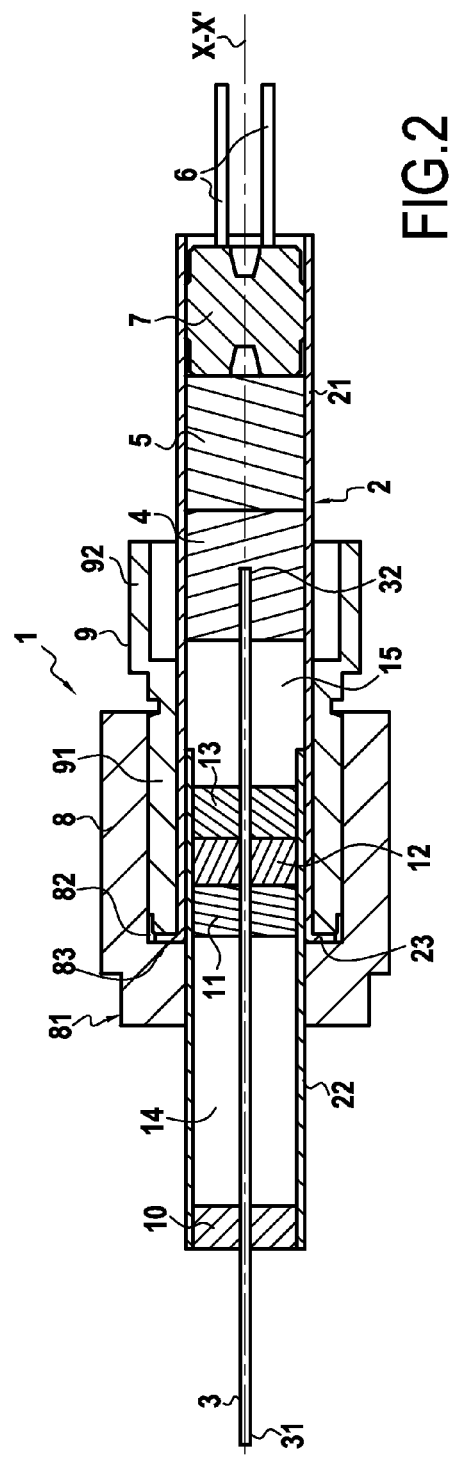

EXHAUST SENSOR FOR AN INTERNAL COMBUSTION ENGINE

This application is a 371 of PCT/FR2012/051860, filed on Aug. 7, 2012, which claims priority to French Application No. 1157224, filed Aug. 8, 2011.

The present invention relates to the technical field of in-line measurement of physical parameters or of chemical element concentrations in the exhaust gas from combustion, such as for example in internal combustion engines or in boilers.

More particularly, the invention relates to an exhaust sensor specially designed to withstand the very high temperature conditions and the aggressive gas in the exhaust line of an internal combustion engine.

In the field of the invention, sensors are already known for measuring the temperature or the concentration of gases such as nitrogen oxide in the exhaust gas stream from internal combustion engines.

Those sensors comprise a metal body acting as a sheath for mounting a sensing element, often made of ceramic, that is housed inside the metal body and that is connected via simple electrical connections to an electronic control unit of the internal combustion engine or to an electronic control dedicated to the sensor.

In the exhaust lines of internal combustion engines, such sensors are subjected to high levels of thermal, chemical, and mechanical stress.

Aggressive gases and condensation can lead to electrical short circuits or open circuits in the electrical connections of sensors inside the bodies of the sensors if complete leaktightness is not guaranteed between the exhaust gases and the inside portion of the sensor, and thus between the body and the sensing element.

Furthermore, on occasion, the temperature of exhaust gas can reach peaks of about 900° C. to 1100° C. The sensors must then withstand such a temperature, both externally and internally, in particular for the purpose of avoiding any melting of the electrical connection circuits that would be likely to take the sensor out of operation.

Furthermore, such exhaust sensors must be as compact as possible in order to be capable of being inserted in the exhaust line, e.g. in the engine compartment of a vehicle, even though the amount of space available in such a compartment is becoming smaller and smaller. The various component elements of sensors, in particular concerning internal connections and gaskets, are not capable of withstanding very high temperatures and must therefore be insulated as much as possible from the temperature inside the exhaust line, with this being made increasingly difficult since the structure of the sensor needs to be both compact and leaktight.

In the state of the art, U.S. Pat. No. 6,672,132 proposes an exhaust sensor for withstanding aggression from exhaust gas. Such an exhaust sensor comprises a protection tube having mounted therein a tubular support body that receives a measurement probe. The measurement probe is mounted in the support body by means of a stack of mutually touching spacers made of ceramic or of glass. Making a tubular support body that is mounted inside a protective tube leads to an exhaust sensor that is bulky and not easy to fabricate. Furthermore, such a design does not make it possible to obtain sufficient thermal decoupling.

The object of the present invention is consequently to provide a novel exhaust sensor structure that provides good leaktightness against exhaust gas and good thermal insulation for the components of the sensor that are sensitive to the temperatures of said exhaust gas.

For this purpose, the present invention provides an exhaust sensor comprising a tubular support body extending around a longitudinal axis and receiving a measurement probe adapted to measure the temperature and/or the concentrations of gases or of molecules inside an exhaust pipe of an internal combustion engine. In the exhaust sensor, a first end of the measurement probe extends beyond a first end of the tubular support body through an opening therein, and a second end of said probe is secured to an electrical connection connector that is housed inside the tubular support body and that fits closely against its walls. The electrical connection connector has electrical connection pins that extend to the outside of the tubular support body through a second end thereof.

According to the invention, the measurement probe is sealed inside the tubular support body of the sensor and is thermally decoupled from the environment outside the body by means of an assembly of spacers made of ceramic and of glass and/or metal that are threaded around the measurement probe and distributed inside the tubular support body between the electrical connection connector and the first end of the tubular support body so as to provide at least two separate cavities, said spacers providing leaktight sealing between the measurement probe and the tubular support body.

Sealing the measurement probe inside the tubular support body of the exhaust sensor of the invention serves both to provide good thermal protection for the electrical connections of the measurement probe in the rear end of the sensor, and also to provide complete leaktightness between the inside of the sensor body and the gases and condensation present in an exhaust pipe. The use of spacers made of ceramic and of glass provides sealing that withstands very high temperatures and that is a poor thermal conductor, while also being compact. This makes it possible to provide internal cavities inside the sensor body that may be filled with gas or evacuated and that therefore provide the best possible thermal insulation between the end of the sensor that is situated in the exhaust pipe and its rear end where its electrical connections are located.

In an embodiment, the spacers are distributed inside the tubular support body in two groups of spacers, a first group providing a partition between the two cavities, and a second group forming a plug at the first end of the tubular support body.

Preferably, the spacers present a melting temperature higher than 500° C. Said spacers can thus withstand the high temperatures in an exhaust pipe of an internal combustion engine.

In an embodiment, at least a first group of spacers comprises at least three juxtaposed spacers comprising a glass spacer interposed between two ceramic spacers, the second group being constituted by spacers made of ceramic only. Such a structure makes it possible in particular to improve the leaktightness of the sensor in the first group of spacers because of the presence of glass that, once it has melted, acts as a binder between the ceramic spacers and the sensor body, penetrating into all of the interstices present between the ceramic spacers and the body of the sensor and between the spacers and the measurement probe, thus avoiding any risk of gas leaking towards the connections.

In an embodiment, the glass spacer of the first group of spacers is made of a material comprising silica prepared in any one of the following particular forms: powder, gel, compacted powder, paste, monolithic glass.

In an embodiment, the glass spacer is capable of wetting the ceramic beads and the tubular support body. The term "wetting" is used herein to mean that once the glass has melted, the glass spacer wets the ceramic spacers and the support body well, i.e. adhesion between the melted glass and the ceramics or the support body is good.

In an embodiment, the spacers of the first group are secured to one another by at least partially melting the glass spacer after the first group of spacers has been inserted in the tubular support body.

In an embodiment, the ceramic spacers include cavities filled with insulating gas.

In an embodiment, the two cavities formed inside the tubular support body are filled with insulating gas. Such an insulating gas may be constituted in particular by air, argon, or indeed nitrogen.

In an embodiment, the two cavities formed inside the tubular support body are prepared in a vacuum.

In an embodiment, the tubular support body is made of a stainless steel selected from the following steels: Inconel 600, Inox 321, Inox 409, Inox 304, Inox 4509, Inox 4521, Inox 4571, Inox 444, or indeed is made of titanium.

In an embodiment, the inside surface of the tubular support body includes abutments for longitudinally stopping the two groups of spacers, which abutments are adapted to facilitate positioning said spacers inside the tubular support body and to enable the two thermal internal decoupling cavities to be provided.

In an embodiment, the sensor of the invention also includes a tapping member for tapping the sensor into an exhaust pipe, said tapping member being threaded over the tubular support body of the sensor.

In the context of the present invention, the term "tapping member" is used to mean a part for fitting the sensor on an exhaust pipe of an internal combustion engine, and in particular enabling the sensor both to be put into place and to be removed.

In this embodiment, the tapping member is made of a metal material and includes peripheral fins for thermally dissipating heat transmitted by an exhaust pipe after the sensor has been tapped into said pipe. The tapping member of the sensor thus acts as a radiator for dissipating heat transmitted to the exhaust sensor by the exhaust pipe and the exhaust gas inside the exhaust pipe, thereby further limiting the amount of heat energy that is transmitted inside the sensor body as far as the electrical connector.

Various other characteristics appear from the description made below with reference to the accompanying drawing, which shows embodiments of the invention as non-limiting examples. In the accompanying figures:

FIG. 1 is a longitudinal section view of an exhaust sensor in accordance with the present invention in a first variant embodiment; and FIG. 2 is a longitudinal section view of an exhaust sensor in accordance with the present invention in a second variant embodiment.

The present invention proposes a novel exhaust sensor structure presenting improved thermal insulation and sealing performance while remaining compact.

The exhaust sensor 1 of the invention comprises a support body 2 receiving a measurement probe 3 adapted to measure the temperature and/or the concentrations of gases or of molecules or of particles inside an exhaust pipe of an internal combustion engine (not shown in the figures).

The support body 2 is of cylindrical tubular shape and it extends along a longitudinal axis X-X'. The tubular support body 2 may be made as a single piece out of a cylindrical tube, or, as in the example shown, it may be made as two cylindrical tube sections 21 and 22 referred to respectively as the lower section and the upper section, that are engaged one in the other along the axis X-X', and that are assembled together, e.g. by welding or by any other analogous technique.

The support body 2 is preferably made of a stainless steel suitable for withstanding very high temperatures, such as Inconel 600.

The measurement probe 3 is constituted by a ceramic strip substantially in the shape of a rectangular parallelepiped having electrodes and/or measurement elements for measuring one or more physical parameters of an exhaust gas. This measurement probe 3 extends inside the tubular support body 2 along its longitudinal axis X-X'.

A first end 31 of the measurement probe projects out from the support body 2 through a first end of the upper section 22 of said support body. This first end 31 is to come into contact with an exhaust stream in an exhaust pipe for the purpose of measuring temperature and/or concentrations of gases or of particles in the exhaust stream. This first end 31 of the measurement probe is optionally provided with protection against the exhaust stream.

At its second end 32, the measurement probe 3 is secured to a connector 4 for providing electrical connection that is housed in the lower section 21 of the tubular support body 2. A separation defining spacer 5 separates this electrical connection connector 4 from a plug 7 for plugging the second end of the tubular support body 2, the spacer and the plug having at least two electrical connection pins 6 extending therethrough from the connector. These electrical connection pins 6 enable the exhaust sensor 1 to be connected, and more particularly they enable the measurement probe 3 to be connected to an electronic driver unit, e.g. an electronic control unit of an internal combustion engine.

Around the tubular support body 2, the exhaust sensor 1 of the invention also has a tapping ring 8 together with a nut 9 for screwing the exhaust sensor 1 into a mounting housing provided for this purpose in the exhaust pipe of an internal combustion engine. The tapping ring 8 and the nut 9 are advantageously threaded over the tubular support body 2, the tapping ring 8 around the upper section 22 of said support body 2 and the screw fastener nut 9 around the lower section 21 of the support body 2. In advantageous manner, the tapping ring 8 includes a cylindrical bearing surface 81 for inserting in and engaging with an orifice provided for that purpose in order to be welded thereto, and an internal cylindrical chamber 82 that opens out towards the section 21 of the tubular support body and that defines an internal annular shoulder 83 for positioning the tapping ring 8 in abutment against a ring 23 that extends radially from the longitudinal axis X-X', projecting from the outside surface of the section 22 of the tubular support body 2. Thus, when the tapping ring 8 is threaded over the section 22, it becomes positioned in an extreme position along the tubular support body 2 that is determined by the ring 23. By acting on the position of the ring 23 secured to the tube 21, it is possible to adjust the insertion height of the exhaust sensor 1 in an exhaust pipe.

Furthermore, the cylindrical chamber 82 formed inside the tapping ring 8 presents a diameter greater than the outside diameter of the section 22 of the tubular support body 2 such as the screw fastener nut 9, which has a first section forming a threaded screw fastener shank 91 and a second section forming a clamping bushing 92. The screw fastener nut 9 may have its screw fastener shank 91 screwed into said cylindrical chamber 82, thus providing a junction between the nut 9 and the tapping ring 8 around the tubular support body 2, the clamping bushing 92 remains accessible outside the tapping ring 8 and the tubular support body 2 in order to enable the sensor to be mounted and screwed in the exhaust pipe.

Exhaust sensors of internal combustion engines are subjected to environments that are severe (corrosive gas, acid, high temperature, steam at high temperature, . . . ) and to toxic gases (CO, NOx, SOx, aromatic rings, . . . ) and also to hydrocarbons.

The various component elements inside such sensors cannot withstand very high temperatures and they need to be thermally decoupled from the temperature that exists inside the exhaust tube. They also need to be protected against any condensation on the internal connections of the sensor, which might lead to short circuits and thus to erroneous measurements, and even in the long term to a loss of contact (e.g. due to corrosion).

The exhaust sensor 1 of the invention seeks to provide resistance to high temperature and sealing between the measurement probe 3 and its tubular support body 2 by means of a structure that encourages thermal decoupling in a medium that is as severe as the exhaust line of an engine, where materials such as resins (epoxy, polyamide, . . . ), fluorocarbon gaskets, . . . , cannot provide such a function.

For this purpose, the exhaust sensor of the invention thus includes special sealing for the measurement probe 3 in the tubular support body 2.

This sealing may be provided in analogous manner either as shown in FIG. 1 or as shown in FIG. 2. It consists in sealing the measurement probe 3 to the tubular support body 2 via an assembly of at least three, and preferably four spacers 10, 11, 12, and 13 that are made of ceramic, of metal, or of glass. These spacers are threaded around the measurement probe 3 and distributed inside the tubular support body 2 between the electrical connection connector 4 and the first end of the tubular support body 2 so as to provide at least two separate cavities 14 and 15 inside the tubular support body 2 between the opening through which the measurement probe 3 projects at the top end of the tubular support body 2 and the electrical connection connector 4.

These two cavities 14 and 15 inside the tubular support body 2 serve to provide thermal decoupling between the first end 31 of the measurement probe 3 that is inside an exhaust pipe, and its second end 32 that is beside the electrical connection connector 4, the decoupling being for the purpose of protecting the electrical connections from the heat of the exhaust stream in which the sensor is placed.

The cavities 14 and 15 formed inside the tubular support body 2 may be filled with an insulating gas such as air, nitrogen, or argon, or indeed they may be prepared in a vacuum, depending on the thermal insulation performance desired for the sensor.

As shown in FIGS. 1 and 2, the spacers 10, 11, 12, and 13 are distributed inside the tubular support body 2 as two groups of spacers, a first group providing a partition between the two cavities 14 and 15, and a second group forming an optionally leaktight plug for the first end of the tubular support body 2.

For the purpose of positioning the two groups of spacers 10, 11, 12, and 13, it is possible to provide positioning abutments on an inside face of the tubular support body 2, the abutments being formed by upsetting material or by lightly stamping the sections 21 and 22 forming the tubular support body 2.

Whatever the embodiment selected, these two groups of spacers 10, 11, 12, and 13 are constituted by a first group of at least two juxtaposed spacers and preferably three juxtaposed spacers 11, 12, and 13 comprising a glass spacer 12 interposed between two ceramic spacers 11 and 13, while the second group is constituted by a spacer 10 of ceramic only or of metal only. These two groups of spacers may be positioned in either order inside the tubular support body 2, as shown in FIGS. 1 and 2.

Thus, in the first embodiment shown in FIG. 1, the first group of three spacers 11, 12, and 13 forms a plug at the top end of the tubular support body 2 while the second group comprising at least one ceramic or metal spacer 10 is located substantially in the middle of said tubular support body 2. In a second variant shown in FIG. 2, the arrangement is inverted, and the first group of three spacers 11, 12, and 13 is placed in the middle of the tubular support body 2, while the second group comprising the spacer 10 forms the plug at the top end of the tubular support body 2.

In a manner that is preferred in the context of the invention, the spacers 10, 11, 12, and 13 all present a melting temperature higher than 500° C. so as to present good resistance to the heat conveyed by an exhaust stream from an internal combustion engine while the sensor 1 is in use. In particular, the ceramic spacers 10, 11, and 13 may be made of a material such as alumina, zirconia, steatite, mullite, or indeed a metal such as Inconel 600, a refractory steel, or titanium.

The glass spacer 12 in the first group of spacers is made of a material comprising silica prepared in one of the following particular forms: powder, gel, compacted powder, paste, or monolithic glass. One of the important properties of this glass spacer 12 is to be capable of wetting the ceramic spacers 11 and 13 of the first group on either side thereof and also of wetting the tubular support body 2 and the measurement probe 3.

In an advantageous manner of the invention, the spacers 11, 12, and 13 of the first group are secured to one another by the glass spacer 12 melting at least in part after the first group of spacers has been inserted inside the tubular support body 2.

The glass spacer 12 may be melted by various means during the fabrication of the exhaust sensor of the invention. In particular, it is possible to envisage melting by heating in an oven, or by heating using induction, microwaves, infrared light, or indeed a laser. During the melting of the glass spacer 12, it is desirable for the ceramic spacers 11 and 13 to be compressed against the glass spacer 12 so that the molten glass fills in any clearance that might have been left for mounting purposes between:

the ceramic spacers 11 and 13 and the tubular support body 2;
the ceramic spacers 11, 13 and the measurement probe 3;
the glass spacer 12 and the tubular support body 2; and
the glass spacer 12 and the measurement probe 3.

Also in advantageous manner, the ceramic spacers 11 and 13 of the first group of spacers may present shapes that encourage melted glass to pass between the tubular support body 2 and themselves, and/or the measurement probe 3 and themselves, thereby serving to guarantee better leaktightness for the assembly.

Once melting has terminated and the glass has set, the measurement probe is held mechanically in the tubular support body 2 and is completely leaktight on either side of the glass spacer 12, thus avoiding any condensation or gas penetrating into the inside of said tubular support body 2.

In a preferred embodiment of the exhaust sensor 1 of the invention, in order to further reduce the transfer of heat towards the electrical connection connector 4, the ceramic spacers 10, 11, and 13 may include cavities filled with an insulating gas or with a vacuum.

This particular construction for the exhaust sensor of the invention provides good leaktightness and thermal decoupling in a space that is as small as possible for the electrical connections of the measurement probe 3, which connections are the most liable to suffer deterioration because of the extreme conditions under which the exhaust sensor is used. This serves to preserve these electrical connections, and in particular to preserve the integrity of the connection connector 4 and of the electrical connection pins 5, and to increase the lifetime and the response performance of the exhaust sensor 1 in comparison with previously known sensors.

Furthermore, it is also advantageous to take advantage of the tapping ring 8 of the exhaust sensor 1 also to diffuse to the air surrounding the sensor the heat that is transmitted in particular by conduction from the exhaust pipe on which the sensor is installed, with this being done by making said tapping ring out of a conductive metal material and by forming cooling fins on the ring in order to increase the heat exchange area of the tapping ring 8 and thus dissipate the heat energy received from the exhaust pipe supporting the sensor 1 via the tapping ring 8 towards the outside instead of transmitting the heat to the tubular support body 2 of the sensor. It should be observed that it is also possible to envisage providing cooling fins on the screw fastener nut 9.

The exhaust sensor 1 of the present invention thus provides increased leaktightness and resistance to high temperatures in a minimum amount of space, thereby providing better overall ability to withstand the extreme operating conditions of exhaust sensors positioned in exhaust circuits of internal combustion engines.

The invention claimed is:

1. An exhaust sensor comprising a tubular support body extending around a longitudinal axis X-X' and receiving a measurement probe adapted to measure the temperature and/or the concentrations of gases, of molecules, or of particles inside an exhaust pipe, in particular of an internal combustion engine, a first end of said measurement probe extending beyond a first end of the tubular support body through an opening therein, and a second end of said measurement probe to be secured to an electrical connection connector housed inside the tubular support body fitting closely against its walls and including electrical connection pins extending outside the tubular support body via a second end thereof, the sensor being characterized in that the measurement probe is sealed inside the tubular support body and is thermally decoupled from the environment outside the body by means of an assembly of spacers made of ceramic or metal, and of glass, the spacers being threaded around the measurement probe and distributed inside the tubular support body between the electrical connection connector and the first end of the tubular support body so as to provide at least two separate cavities, said spacers providing leaktight sealing between the measurement probe and the tubular support body.

2. An exhaust sensor according to claim 1, characterized in that the spacers are distributed inside the tubular support body in two groups of spacers, a first group providing a partition between the two cavities, and a second group forming a plug at the first end of the tubular support body.

3. An exhaust sensor according to claim 2, characterized in that the spacers present a melting temperature higher than 500° C.

4. An exhaust sensor according to claim 2, characterized in that at least a first group of spacers comprises at least three juxtaposed spacers comprising a glass spacer interposed between two ceramic spacers, the second group being constituted by spacers made of ceramic or metal only.

5. An exhaust sensor according to claim 4, characterized in that the glass spacer of the first group of spacers is made of a material comprising silica prepared in any one of the following particular forms: powder, gel, compacted powder, paste, monolithic glass.

6. An exhaust sensor according to claim 4, characterized in that the glass spacer is capable of wetting the ceramic spacers, the tubular support body, and the measurement probe.

7. An exhaust sensor according to claim 4, characterized in that the spacers of the first group are secured to one another by at least partially melting the glass spacer after the first group of spacers has been inserted in the tubular support body.

8. An exhaust sensor according to claim 1, characterized in that the ceramic spacers include cavities filled with an insulating gas.

9. An exhaust sensor according to claim 1, characterized in that the two cavities formed inside the tubular support body are filled with insulating gas.

10. An exhaust sensor according to claim 1, characterized in that the two cavities formed inside the tubular support body are prepared in a vacuum.

11. An exhaust sensor according to claim 1, characterized in that the tubular support body is made of a stainless steel, of Inconel, or of titanium.

12. An exhaust sensor according to claim 1, characterized in that the inside surface of the tubular support body includes abutments for longitudinally stopping the two groups of spacers, which abutments are adapted to facilitate positioning said spacers inside the tubular support body and to enable the two thermal internal decoupling cavities to be provided.

13. An exhaust sensor according to claim 1, characterized in that it includes a tapping member for tapping the sensor into an exhaust pipe, said tapping member being threaded over the tubular support body of the sensor.

14. An exhaust sensor according to claim 13, characterized in that the tapping member is made of a metal material and includes peripheral fins for thermally dissipating heat transmitted by an exhaust pipe after the sensor has been tapped into said pipe.

* * * * *